(12) United States Patent
Ingber (10) Patent No.: US 8,309,897 B2
(45) Date of Patent: Nov. 13, 2012

(54) OPTICAL MEASUREMENT ARRANGEMENT

(75) Inventor: Gal Ingber, Oranit (IL)

(73) Assignee: Pocared Diagnostics Ltd. (IL)

( * ) Notice: Subject to any disclaimer, the term of this patent is extended or adjusted under 35 U.S.C. 154(b) by 330 days.

(21) Appl. No.: 12/697,618

(22) Filed: Feb. 1, 2010

(65) Prior Publication Data

US 2010/0200728 A1     Aug. 12, 2010

Related U.S. Application Data

(60) Provisional application No. 61/150,430, filed on Feb. 6, 2009.

(51) Int. Cl.
| | |
|---|---|
| G01J 1/32 | (2006.01) |
| G01N 35/02 | (2006.01) |
| G01N 21/03 | (2006.01) |
| G01N 33/539 | (2006.01) |

(52) U.S. Cl. ......... 250/205; 356/246; 356/319; 436/171
(58) Field of Classification Search .................. 250/205, 250/201.1; 356/246, 300, 319–334; 436/164, 436/171, 172
See application file for complete search history.

(56) References Cited

U.S. PATENT DOCUMENTS

| | | | |
|---|---|---|---|
| 4,360,360 A | 11/1982 | Chiknas | |
| 4,406,547 A | 9/1983 | Aihara | |
| 4,449,821 A * | 5/1984 | Lee | ............................... 356/319 |
| 4,477,186 A | 10/1984 | Carlson | |
| 4,509,856 A | 4/1985 | Lee | |
| 4,565,447 A * | 1/1986 | Nelson | ........................... 356/319 |
| 4,701,607 A * | 10/1987 | El-Hanany et al. | ............ 250/205 |
| 4,829,533 A * | 5/1989 | Hallberg et al. | ......... 372/29.021 |
| 4,873,993 A | 10/1989 | Meserol et al. | |
| 5,029,245 A * | 7/1991 | Keranen et al. | ................ 250/205 |
| 5,314,825 A | 5/1994 | Weyruch | |
| 5,578,269 A | 11/1996 | Yarenmko | |
| 5,605,665 A | 2/1997 | Clark et al. | |
| 6,515,745 B2 | 2/2003 | Vurens et al. | |
| 6,559,941 B1 * | 5/2003 | Hammer | ....................... 356/319 |
| 6,773,922 B2 | 8/2004 | Jeng et al. | |
| 6,831,740 B2 * | 12/2004 | Herzinger et al. | ............. 356/319 |
| 7,206,620 B2 | 4/2007 | Erickson et al. | |
| 7,277,175 B2 | 10/2007 | Thompson et al. | |
| 7,299,079 B2 | 11/2007 | Rebec et al. | |
| 7,303,922 B2 | 12/2007 | Jeng et al. | |

(Continued)

FOREIGN PATENT DOCUMENTS

WO     2005/124365 A2     12/2005

(Continued)

*Primary Examiner* — John Lee
(74) *Attorney, Agent, or Firm* — The Webb Law Firm (57) ABSTRACT

A method and device for enhancing the power correction of optical measurements in an optical measurement arrangement, the steps including: providing a light source for producing a light beam; splitting the light beam into two beams; directing a first split light beam through an interrogation area and into an optics separation device; directing the light beams from the optics separation device and a second split light beam representing the intensity of the illumination of the main light beam of the light source into cells of a detector array; measuring and assessing the information obtained in the cells; and using this information to calculate the corrected value for the cells receiving the light beams from the optics separation device in order to adjust the power for the intensity of the light beam of the light source and/or to correct the intensity of the light beams from the interrogation area.

4 Claims, 4 Drawing Sheets

U.S. PATENT DOCUMENTS

| | | |
|---|---|---|
| 2005/0110980 A1 | 5/2005 | Maehara et al. |
| 2005/0110989 A1 | 5/2005 | Schermer et al. |
| 2005/0271550 A1 | 12/2005 | Talmer et al. |
| 2006/0013729 A1 | 1/2006 | Carey et al. |
| 2007/0037135 A1 | 2/2007 | Barnes et al. |
| 2007/0189925 A1 | 8/2007 | Blecka et al. |
| 2008/0100837 A1* | 5/2008 | de Boer et al. .......... 356/326 |
| 2008/0297796 A1 | 12/2008 | Lukas et al. |
| 2008/0297798 A1 | 12/2008 | Wyssen |
| 2009/0067280 A1 | 3/2009 | Ammann et al. |
| 2010/0200728 A1* | 8/2010 | Ingber .......... 250/205 |

FOREIGN PATENT DOCUMENTS

| | | |
|---|---|---|
| WO | 2007039524 A2 | 4/2007 |
| WO | 2007085715 A1 | 8/2007 |
| WO | 2009/049171 A2 | 4/2009 |

* cited by examiner

OPTICAL MEASUREMENT ARRANGEMENT

CROSS REFERENCE TO RELATED APPLICATIONS

The present cross-reference application claims priority to Provisional Application No. 61/150,430, entitled "Optical Measurement Arrangement", filed on Feb. 6, 2009, which is herein incorporated by reference in its entirety.

BACKGROUND OF THE INVENTION

1. Field of the Invention

This invention relates to an optical measurement arrangement which includes a detector array assembly having a plurality of detector elements. More specifically, the invention relates to an optical measurement arrangement which corrects the power changes occurring in the optical measurement arrangement when performing the optical measurement of a signal which is a result of a light illumination. The optical measurement arrangement of the invention may find particular application in an optical analyzer for analyzing urine samples.

2. Description of Related Art

In general, current-day practice for identifying micro-organisms, e.g., bacteria in urine specimens involves a complex, lengthy and expensive process for identifying and specifying micro-organisms in microbiology labs. In the current process, the specimens are accepted into the lab. These specimens are then sorted and labeled and then they are inoculated onto blood agar medium using sterilized loop. The specimens are then inserted into a dedicated incubator for a 24-hour period. A day later, the lab technicians screen the specimens for positive and negative cultures. In general, most of the cultures are negative and they are manually reported. The organisms for the positive cultures are isolated and suspended in a biochemical fluid. This involves suspension, dilution, vortexing and turbidity measurements resulting in biochemical waste products. The cultures are then subjected to a species identification and antibiotics susceptibility testing exposing the suspensions to multiple reagents. After another 6- to 24-hour incubation period, the findings are interpreted and reported by lab technicians. This entire process generally takes 11 steps and 50 hours to obtain specimen results and the process is labor intensive.

WIPO Publication No. WO 2009/049171 filed Oct. 10, 2008 and entitled "SYSTEM FOR CONDUCTING THE IDENTIFICATION OF BACTERIA IN URINE" discloses a system for identifying bacteria in urine samples and includes: 1) a disposable cartridge or holder for holding disposable components including a centrifuge tube, two pipette tips with a different volume capacity and an optical cup or cuvette; 2) a sample processor for processing or preparing the urine samples; and 3) an optical analyzer for analyzing the processed urine samples. The disposable cartridge with its four components is used in the sample processor and the optical cup or cuvette, in particular, is used in the optical analyzer.

In this system of the aforementioned WIPO Publication No. WO 2009/049171 the urine samples are contained within disposable cartridges which hold disposable components, i.e., a centrifuge, two pipette tips with a different volume and an optical cuvette. The cartridges are bar coded and tied in with the patient's ID. The cartridges are inserted in a magazine which is then inserted into a sample processor which processes the specimens. The prepared specimens are injected into the optical cuvettes which are then inserted into an optical analyzer which analyzes the specimens. The optical analyzer analyses and generates the complete results enabling ultimate treatment of the bacteria. The system does not require a sophisticated operator and gives rapid results. The system increases efficiency, improves workload, saves time and money and is easy to operate. The sample preparation can be performed in parallel with the specimen analysis process and from 1 to 50 specimens can be analyzed simultaneously.

This system of WIPO Publication No. WO 2009/049171 includes a plurality of disposable cartridges for holding a plurality of disposable components including a centrifuge tube, a first pipette tip with a 1 ml volume; an optical urine sample cuvette, and a second pipette tip with a 0.5 ml volume; a sample processor for receiving the plurality of disposable cartridges and configured to process and prepare the urine sample of each disposable cartridge and to transfer the urine samples into the respective optical cuvette of each of the disposable cartridges; and an optical analyzer for receiving the optical cuvettes containing the processed urine samples and analyzing and generating the specimen results. The entire procedure for processing the urine specimens in the sample processor and analyzing them in the optical analyzer takes about 20 minutes for a single specimen and up to 2 hours for 50 specimens.

A related method for identifying the type of micro-organism in a urine sample includes the steps of obtaining a urine sample; passing the urine sample through an eleven micron filter; obtaining a 2 ml sample of the filtered urine and placing it into a centrifuge tube; obtaining a 1,000,000:1 dilution of the dissolved materials in the urine retaining bacteria in the urine sample by centrifuging the 2 ml sample at about a 12,000 g-force, decanting about 95% of the fluid in the centrifuge tube, replacing the decanted solution with a saline solution and repeating these steps about five times; transferring the final solution into an optical cup; subjecting the optical cup to an optical analysis having optics which include exciting the urine sample with different wavelengths, collecting and detecting the fluorescent emissions; and directing the fluorescent emissions into a spectrometer which may be part of an optical analyzer of the system of WIPO Publication No. WO 2009/049171.

The optical analyzer used in the aforementioned WIPO Publication No. WO 2009/049171 may include an optical measurement arrangement for optically analyzing the bacteria in urine samples. Currently, when performing an optical measurement of a signal, which is a result of a light source, e.g., a UV light source, the signal will change with a change in the intensity of the light illumination; however, this change does not reflect a change in the measurement variable, e.g. the bacteria in the sample. Previous attempts for correcting the power changes to signals represented by the intensity of the light in an optical measurement arrangement involved splitting the illumination beam into at least a first split beam and a second split beam and then measuring the changes in the second split beam by using a detector assembly, such as a photodiode or PMT (photomultiplier tube). Although the intensity of the second split beam, which is measured by the detector assembly, may represent a change in the first split beam, this intensity of the second split beam will also be affected by any changes occurring in the detector assembly due to factors such as aging, temperature and spectral and/or intensity responses in the detector assembly. Thus, a correction to the intensity of the signal represented by the first split illumination beam based on the intensity of the second split beam being detected by the detector assembly of the prior art optical measurement arrangements, will introduce errors into the power correction to the intensity signal of the illumination beam of these optical measurement arrangements.

Examples of optical measurement arrangements are disclosed in U.S. Pat. Nos. 6,515,745; 6,559,941; 6,773,922; 7,206,620; 7,299,079; and 7,303,922.

There is a need in the art to enhance the power correction to a light source of an optical measurement arrangement by providing a correction signal to the illumination beam that is free from errors existing in the detector assembly used to measure the intensity of the illumination beam generated by the light source.

SUMMARY OF THE INVENTION

The optical measurement arrangement of the present invention has met this need. The optical measurement arrangement of the present invention relates to a device and a method for optimizing the power correction to the light source used as a signal in an optical measurement arrangement. The method includes the steps of: 1) providing a light source for producing a light beam; 2) directing the light beam into a beam splitting device to produce a first split light beam and a second split light beam; 3) directing the first split light beam into a region of interest, e.g. an interrogation area; 4) collecting light from the region of interest and directing it to an optics separation device for separating the first split light beam into several light beams which are detected by the detection elements, e.g. cells of a detector array assembly; 5) while performing steps 3) and 4), directing the second split light beam into a detection element, e.g. cell of the detector array assembly; 6) measuring and assessing the information obtained in the detection elements of the detector array assembly that received the light beams of the first split light beam and the information obtained in the detection element of the detector array assembly that received the second split light beam; and 7) using the information obtained in step 6) to adjust the power for the light beam of the light source and/or to correct the intensity of the light beam of the region of interest.

The device includes a light source for producing a light beam; a beam splitting device for splitting the light beam into a first split light beam and a second split light beam; an interrogation area for receiving the first split light beam; an optics separation device for separating the light generated from the first split light beam into light beams; a detector array assembly having a plurality of detection elements, e.g. cells for receiving the light beams from the optics separation device and for receiving the second split light beam; and measurement means for assessing the information obtained from the detection elements of the detector array assembly which received the light beams from the optics separation device and the information obtained from the detection element of the detector array assembly which received the second split light beam and for creating an output signal used for adjusting the power for the light beam of the light source and/or for correcting the intensity of the light beams from the interrogation area based on the information obtained from the detection elements of the detector array assembly.

It is therefore an aspect of the invention to provide an optical measurement arrangement which includes a detector array assembly and a measuring device for measuring and assessing the intensity of a first split beam light represented in several detection elements of a detector array assembly and the intensity of a second split beam light represented in a detection element of the same detector array assembly and using this information to adjust the power for the light beam of the light source and/or to correct the intensity of the light beam of the light source from a region of interest, e.g. an interrogation area, in an optical measurement arrangement.

It is a further aspect of the invention to provide a method and device for correcting power changes in an optical measurement arrangement by using the same detector array assembly to detect the observed light and to detect the intensity of the illumination of the main light beam of the light source.

Yet a further aspect of the invention is to provide a method and device for detecting the changes in the intensity of the illumination of the light beam generated by a light source in an optical measurement arrangement, which device has the same characteristics as the detector used to measure the observed signal or signals.

These and other aspects and advantages of the invention will be made apparent from the following description taken together with the drawings.

DETAILED DESCRIPTION OF THE INVENTION

The present invention will be described with reference to the accompanying drawings where like reference numbers correspond to like elements. The optical measurement arrangement of the present invention may be used in the optical analyzer described in a system for conducting the identification and quantification of bacteria in urine samples such as that disclosed in the above-discussed WIPO Publication No. WO 2009/049171, filed October 10, 2008, which is incorporated herein by reference in its entirety.

Figure 1:
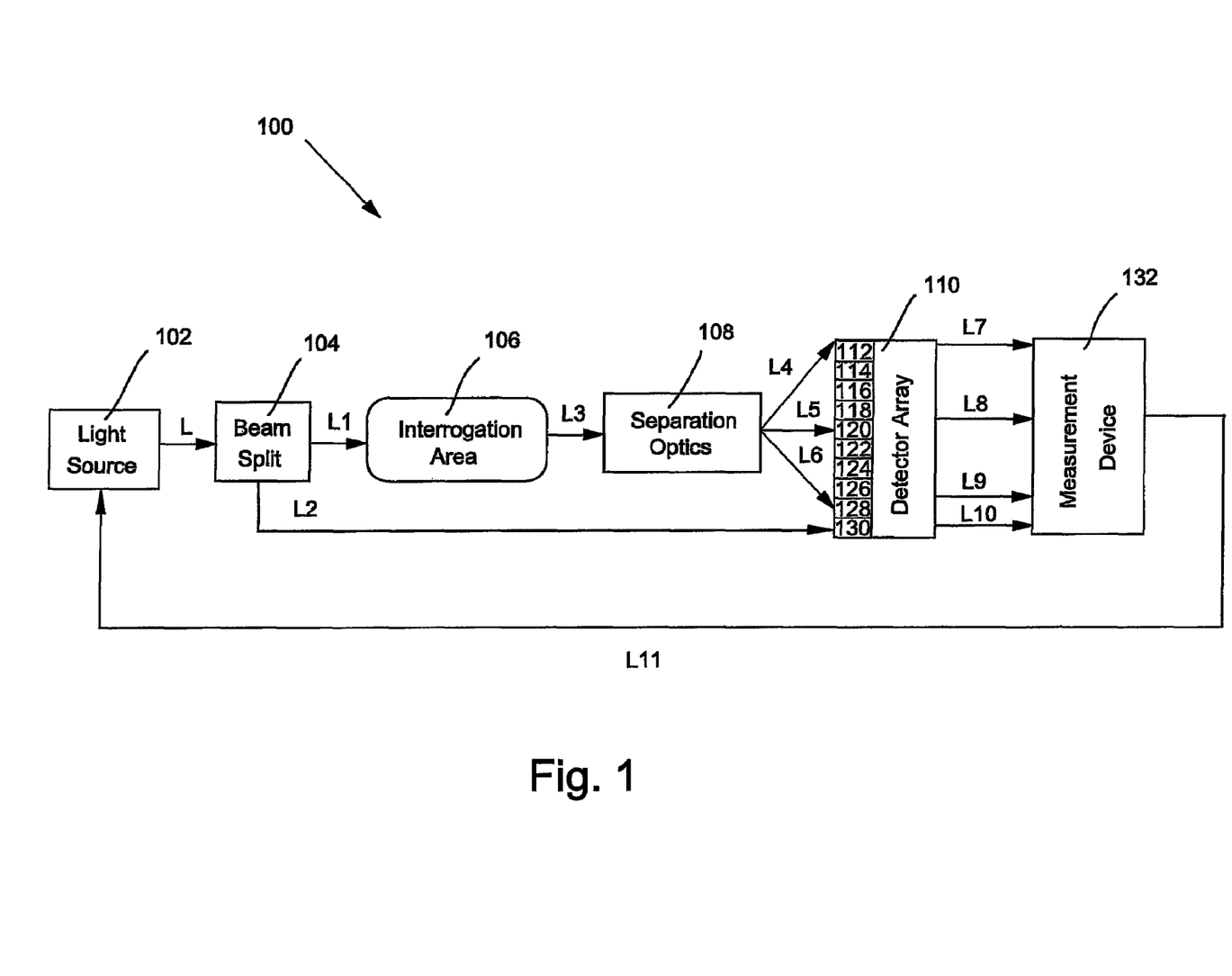
FIG. 1 is a schematic view illustrating an optical measurement arrangement of the present invention, which optionally, may be used in a system for conducting the identification of bacteria in urine samples.

As stated hereinabove, FIG. 1 is a schematic illustrating an optical measurement arrangement of the present invention which optionally may be used in the system for conducting the identification of bacteria in urine samples. In this instance, the optical measurement arrangement 100 may be used in the optical analyzer 16 shown in FIG. 2 and further discussed below. This optical analyzer is also shown and discussed in detail in WIPO Publication No. WO 2009/049171.

As shown in FIG. 1, an optical measurement arrangement 100 includes a light source 102, a beam splitter device 104, an interrogation area 106, a separation optics device 108 and a detector array assembly 110 that has a plurality of detection elements, e.g., cells, 112, 114, 116, 118, 120, 122, 124, 126, 128 and 130.

As shown in FIG. 1, a main light beam indicated at L is generated by the light source 102, which may be any suitable light source, for example, a lamp or laser. The main light beam L is directed into a device which splits the main light beam L into a first split light beam indicated at L1 and a second split light beam indicated at L2, representing the intensity of the illumination of the main light beam L of light source 102. This device may be a beam splitter or it may be a fiber optic coupler. The first split light beam L1 is first directed into the interrogation area 106 which may be a device for measuring fluorescence, transmittance or reflectance of this first split light beam L1 and then directed into the separation optics device 108 which separates the light coming from the interrogation area indicated at L3 into a spatial pattern according to wavelength or polarization. An example of a spatial pattern is represented in FIG. 1 by light rays L4, L5 and L6. These light rays L4, L5 and L6 are directed to and are received by one or more detection elements 112, 114, 116, 118, 120, 122, 124, 126, and 128 of detector array assembly 110.

While light rays L4, L5 and L6 are being received by detection elements 112, 114, 116, 118, 120, 122, 124, 126, and 128, the second split light beam L2 is directed to and received by detection element 130 of detector array assembly 110. The detector array assembly 110 may be a CCD or a photodiode array. Still referring to FIG. 1, a measurement device 132 receives the signals L7, L8 and L9 (the observed light) from detection elements 112, 114, 116, 118, 120, 122, 124, 126, and 128 and also receives the signal L10 from detection element 130 generated by light beam L2, representing the intensity of the illumination of the main light beam L of light source 102.

The measurement device 132 then measures and assesses the signal of the observed light in detection elements 112, 114, 116, 118, 120, 122, 124, 126, and 128 and the intensity of beam L2 of light source 102 in detection element 130 and uses this information to correct the information in cells 112, 114, 116, 118, 120, 122, 124, 126, and 128 for intensity variation of the light beam L generated in light source 102 or adjust the power of light source 102 as indicated by light or signal L11, such as a control signal, which is an output of measurement means 132 and an input to light source 102. Even though L-L11 are referred to as light beams, it is to be appreciated that these light beams L-L11 are converted in a customary manner through the several devices in FIG. 1 into signals having a certain strength which is equated to the intensity of the respective light beams associated with the several devices of FIG. 1.

From the above, it can be appreciated that a power correction of the optical measurements of the optical measurement arrangement 100 of the present invention may be enhanced by using part of the detector array assembly 110, i.e. detection element 130 to measure the intensity of the illumination of the main light beam L of light source 102 by directing the second split light beam L2 into detection 130 of the detector array assembly 110 and using this information based on the intensity of the light source 102 to cell 130 to calculate the corrected value for cells 112, 114, 116, 118, 120, 122, 124, 126, and 128 or to alter the power of the light source 102.

Figure 2:
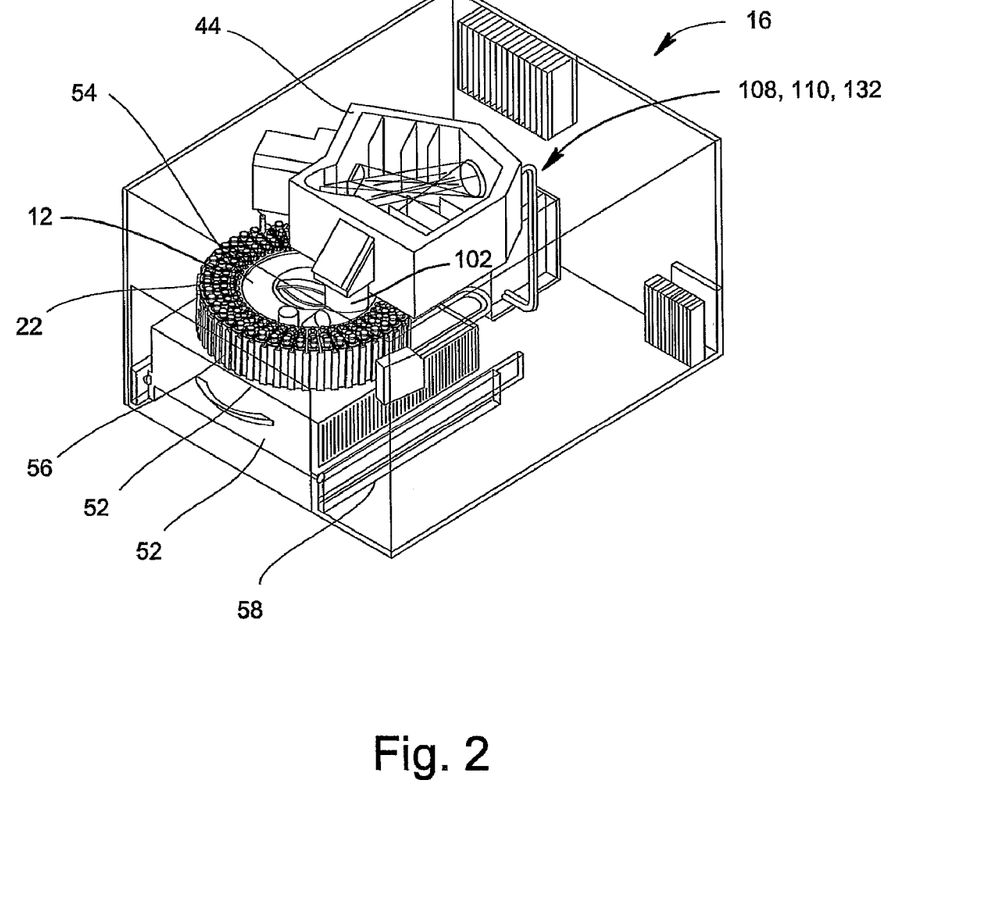
FIG. 2 is a perspective view of an optical analyzer in which the optical measurement arrangement of the invention may be used.

FIG. 2 shows one type of optical analyzer 16 in which the optical measurement arrangement 100 of the invention may be used.

The optical analyzer 16 of FIG. 2 will now be briefly described. The optical analyzer 16 includes an optics system 44, a thermal control unit (not shown), a drawer 50 which has a rotatable table 52 which receives, supports, and rotates a magazine 54 containing a plurality of holders 56 for receiving the disposable cartridges 12 in which cups or cuvettes 22 contain the processed urine samples which are to be analyzed, and a bar code reader 58.

As can be appreciated, a cartridge 12 that has the cups or cuvettes 22 containing the processed urine sample for optical analysis are placed into the holders 56 of the magazine 54. FIG. 2 illustrates the magazine 54 mounted on the rotatable table 52 being loaded into the optical analyzer 16. In this device, drawer 50 is pulled out manually for the loading and unloading of magazine 54. Drawer 50 contains the thermal control unit (not shown) and a drive mechanism (not shown). Alignment features on the magazine 54 and drawer 50 allow the operator to orient the magazine 54 properly on the drive mechanism and the thermal control unit when the magazine 54 is loaded onto the rotatable table 52. Once the drawer 50 and magazine 54 are manually inserted into the optical analyzer 16, the drive mechanism rotates the magazine 54 at which time a bar code reader station 58 inventories the samples. An operator can access the optical analyzer 16 when a user interface indicates that all the samples in the cups or cuvettes 22 have been analyzed and drawer 50 is prevented from being opened when any of the components of optical analyzer 16 are moving or when the UV light sources of the optics system 44 are on.

FIG. 2 illustrates the magazine 54 on rotatable table 52 while being positioned within optical analyzer 16. The optical analyzer 16 further includes a mechanical locking system (not shown) which positions the drawer 50 accurately with respect to the optics system 44. The drive mechanism is configured to automatically rotate the magazine 54 to position each cartridge 12 into the bar code reader station 58 and into precise alignment with the optics system 44. A second mechanical locking system (not shown) is used to secure each cup or cuvette 22 in its proper positioning relative to the optics system 44 for optical analysis.

Figure 3:
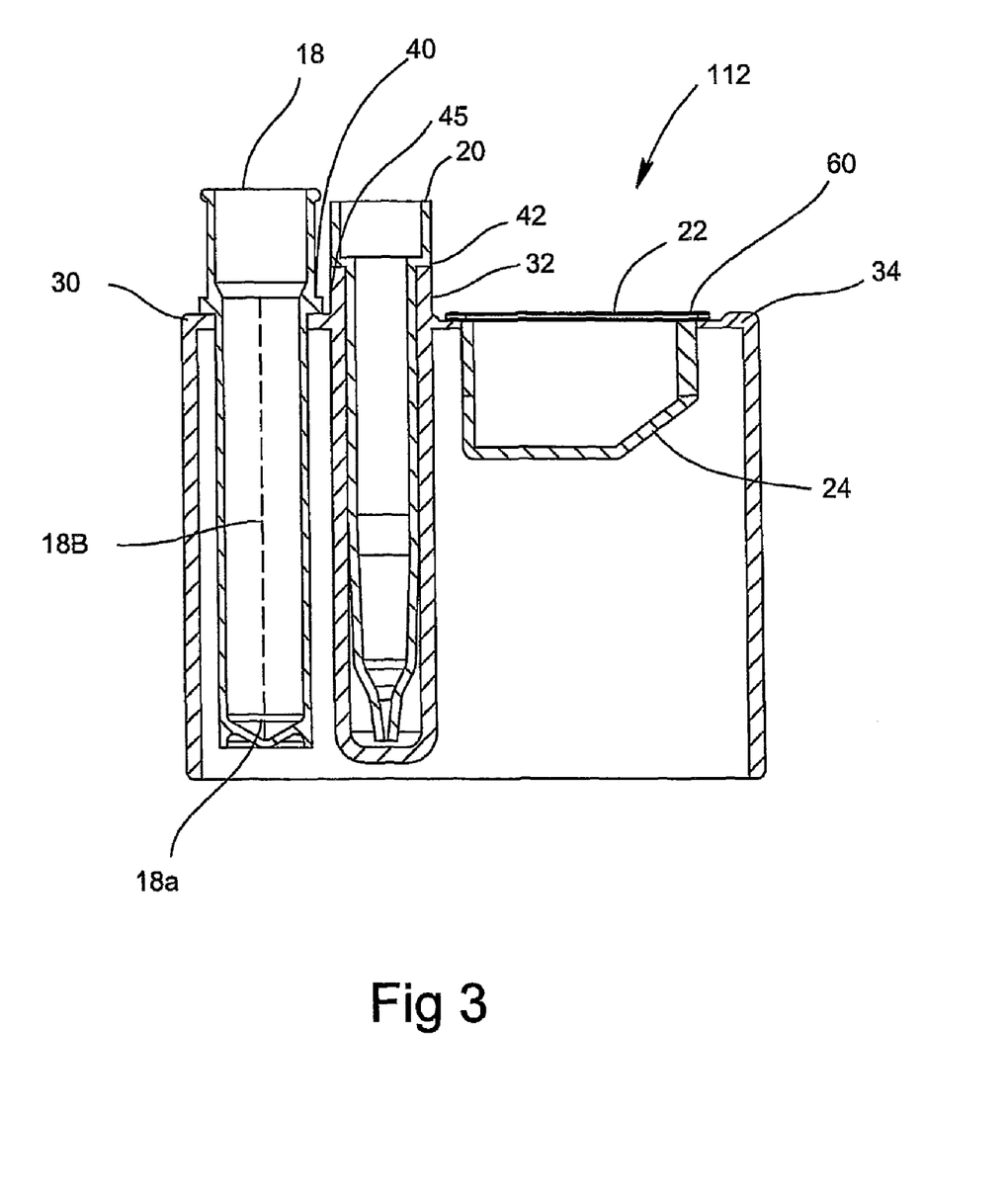
FIG. 3 is a cross-sectional side view illustrating one of the disposable cartridges of FIG. 2 and the disposable components including an optics cup.
Figure 4:
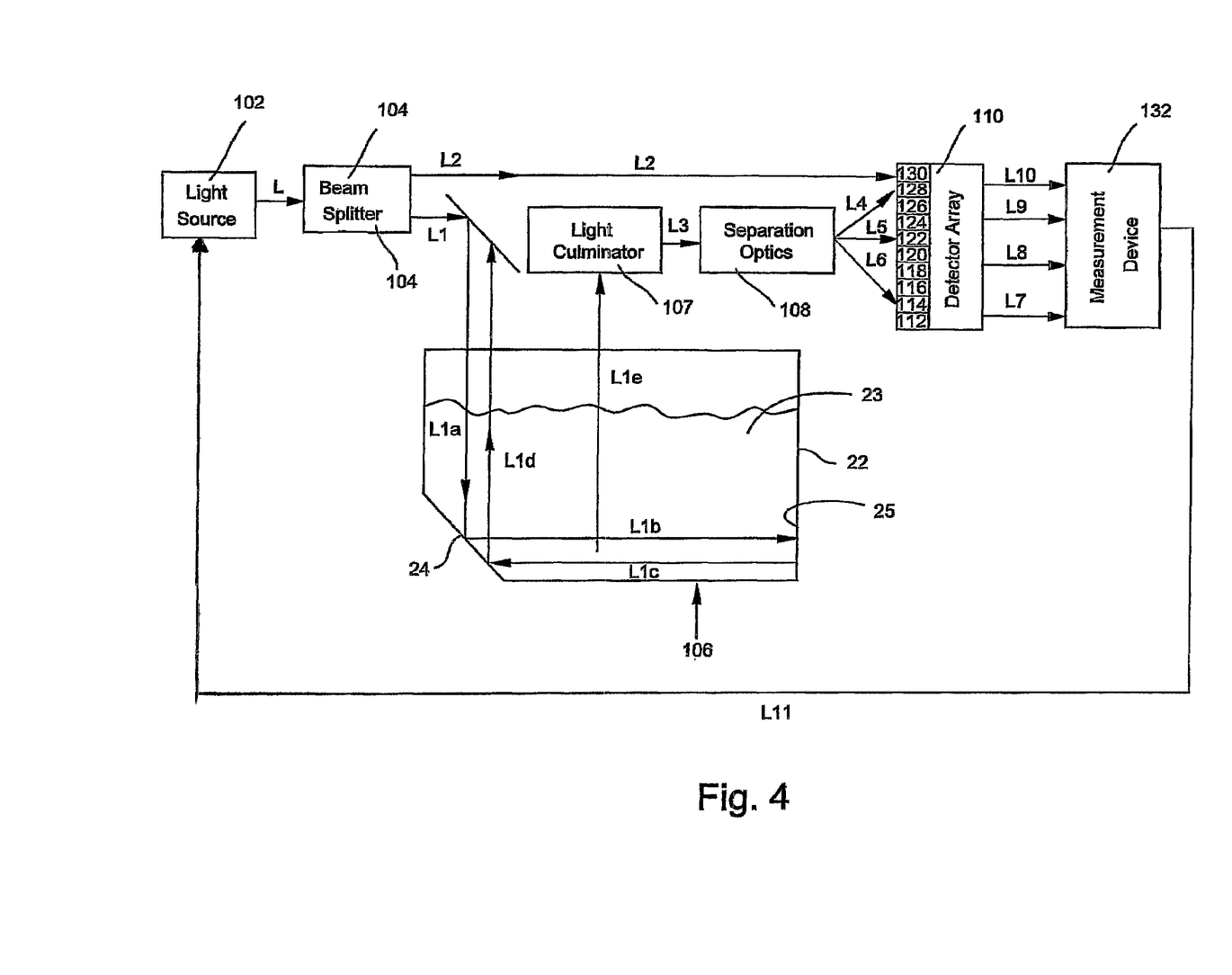
FIG. 4 is a schematic view illustrating in more detail the movement of the light beam through the optics cup of FIGS. 2 and 3 and through the components of the measurement arrangement of FIG. 1.

Reference is now made to FIGS. 3 and 4 which illustrate in more detail the movement of the light beam through a sample and subsequently through the optical measurement arrangement of the invention. FIG. 3 shows a cross-sectional side view of one type of disposable cartridge 12 that can be used in the optical analyzer 16 of FIG. 2 for conducting the identification and qualification of contaminants, e.g., micro-organisms, e.g., bacteria in samples, e.g., urine samples. Disposable cartridge 12 contains and carries several disposable components which include a centrifuge tube 18, a pipette tip 20 and an optics cup or cuvette 22. The centrifuge tube 18 is a container that has an elongated body 18b with a tapered end indicated at 18a. In general, the centrifuge tube 18 initially contains the sample and the pipette tip 20 may be used to dilute the dissolved sample constituents and then transfer the diluted urine sample into the optics cup or cuvette 22 for optical analysis. The disposable cartridge 12 and its disposable components 18, 20 and 22 may be made of an ABS plastic material which is easily injection molded and inexpensive to manufacture.

Still referring to FIG. 3, the disposable components 18, 20 and 22 are each contained within separate compartments 30, 32 and 34, respectively, of the disposable cartridge 12. As is shown, the bottom of compartment 32 which receives and carries the pipette tip 20 is closed so that any drip from the pipette tip 20 will not contaminate the surface below the disposable cartridge 12. Components 18 and 20 are suspended within its respective compartment 30, 32 via a lip 40, 42, respectively. Lips 40 and 42 are attached to its respective component 18 and 20, and are supported by a top surface 45 of disposable cartridge 12. In a similar manner, optics cup or cuvette 22 is suspended within its respective compartment 34 via a flange 60 of optics cup or cuvette 22 which the flange 60 is supported by the top surface 45 of disposable cartridge 12. The compartments 30 and 32 are generally cylindrical shaped and extend substantially the length of centrifuge tube 18 and pipette 20. Compartment 34 for positioning and supporting optics cup or cuvette 22 is substantially enclosed within the disposable cartridge 12 and has a configuration similar to that of optics cup or cuvette 22.

The optics cup or cuvette 22 is a container and preferably includes a reflective coating or layer to assist in the optical analysis. In particular, an inner surface of optics cup or cuvette 22 is coated with a reflective material or contains a layer of reflective material. The optics cup or cuvette 22 may be made of a non-reflective material, for example, an ABS plastic material or glass or it may be made of a metallic material, e.g., aluminum. In the latter instance, that is, if the optics cup or cuvette 22 is made of a non-reflective material, it may be coated with or layered with the reflective material. Alternatively, in the manufacturing of the optics cup or cuvette 22, the layer of reflective material may be incorporated onto the plastic or glass. As shown in FIGS. 3 and 4, the optics cup or cuvette 22 includes the lower tapered area indicated at 24 in order to assist with the optical analysis of the specimen, and it is anticipated that the UV-light source provided in an optical analysis be directed into the optics cup or cuvette 22 for the optical analysis of the specimen, more about which is discussed below in relation to FIG. 4.

FIG. 4 shows the movement of the light beam L through a cuvette 22 and the optical measurement arrangement 100 according to the invention. The light beam is generated by the light source 102 and enters into beam splitter 104 to form the first light beam L1 and the second light beam L2. The second light beam L2 is directed to the detector array 110 as previously discussed. The first light beam L1 is directed into the cuvette 12 or interrogation area 106, and subsequently into a biological sample 23 contained therein. For the purpose of discussion, the interrogation area 106 shown in FIG. 1 also includes the light culminator 107. This first light beam L1 can be redirected into the cuvette 12 through the use of a lens, mirror, or any other well known device. The first split beam L1 contacts the mirror and is redirected into the biological sample as indicated at L1a. The beam L1a contacts the lower tapered area 24, causing the beam, indicated by L1b, to move through the sample and contact inner wall surface 25. This contact then causes the light beam to be again redirected, as indicated by L1c, back through the sample. Light beam L1c then contacts the lower tapered area 24 which causes it to be reflected out of the sample, as indicated by L1d. Light generated in the sample is emitted out of the sample, as shown by L1e, into a light culminator 107. The light culminator 107 collects and redirects the emitted fluorescent light through a series of filters and lens to gather and redirect the light to the separation optics device 108, as indicated by L3, for separating at 108 and subsequent processing through the detector array 110 and the measurement device 132 as discussed above.

It can be appreciated that the optical analyzer 16 of FIG. 2 is only one type of analyzer in which the optical measurement arrangement 100 of the present invention may be used and that the present invention may be used in other types of optical analyzers for measuring and correcting power changes when performing optical measurement of a signal which is a result of light illumination.

The present invention has been described with reference to the preferred embodiments. Obvious modifications and alterations will occur to others upon reading and understanding the preceding detailed description. It is intended that the invention be construed as including all such modifications and alterations.

The invention claimed is:

1. A method for optimizing the power correction to the light intensity used as a signal in an optical measurement arrangement, the steps comprising:
   a) providing a light source for producing a light beam;
   b) directing the light beam into a beam splitting device to produce a first split light beam and a second split light beam;
   c) directing the first split light beam through at least an interrogation area and an optics separation device for separating the first split light beam into one or more light beams;
   d) providing a detector array assembly having a plurality of detection elements for receiving the one or more light beams of the first split light beam and the second split light beam;
   e) directing the one or more light beams of the first split light beam and the second split light beam into one of the plurality of detection elements of the detector array assembly to provide information regarding the detected light of the first and second split light beams;
   f) measuring and assessing the information obtained in at least the detection elements of the detector array assembly which received the one or more light beams of the first split light beam and the information obtained in one of the plurality of detection elements of the detector array assembly which received the second split light beam; and
   g) using this information obtained in step f) to adjust an optical power level of the light source to adjust the intensity level of the light beam of the light source.

2. An optical measurement arrangement comprising:
   a light source for producing a light beam;
   a beam splitting device for splitting the light beam of the light source into a first split light beam and a second split light beam;
   an optics separation device for separating the first split light beam into one or more separated light beams;
   a detector array assembly having a plurality of detection elements for receiving one or more light beams of the first split light beam and the second split light beam to provide information regarding the detected light of the first and second split light beams; and
   a measuring device for measuring and assessing the information obtained in the detection element of the detector array assembly receiving the second split light beam and the information obtained in the detection elements of the detector array assembly receiving the one or more separated light beams of the first split light beam and for using the results of this measurement to adjust the light beam of the light source.

3. A method for optimizing the power correction to the light intensity used as a signal in an optical measurement arrangement, the steps comprising:
   a) providing a light source for producing a light beam;
   b) directing the light beam into a beam splitting device to produce a first split light beam and a second split light beam;
   c) directing the first split light beam through at least an interrogation area and an optics separation device for separating the first split light beam into one or more light beams;
   d) providing a detector array assembly having a plurality of detection elements for receiving the one or more light beams of the first split light beam and the second split light beam to provide information regarding the detected light of the first and second split light beams;

e) directing the one or more light beams of the first split light beam and the second split light beam into one of the plurality of detection elements of the detector array assembly;
f) measuring and assessing the information obtained in at least the detection elements of the detector array assembly which received the one or more light beams of the first split light beam and the information obtained in one of the plurality of detection elements of the detector array assembly which received the second split light beam; and
g) using this information obtained in step f) to correct at least an intensity level of the first light beam being supplied to the interrogation area.

4. An optical measurement arrangement comprising:
a light source for producing a light beam;
a beam splitting device for splitting the light beam of the light source into a first split light beam and a second split light beam;
an interrogation area for receiving the first split light beam,
an optics separation device for separating the first split light beam into one or more separated light beams;
a detector array assembly having a plurality of detection elements for receiving one or more light beams of the first split light beam and the second split light beam to provide information regarding the detected light of the first and second split light beams; and
a measuring device for measuring and assessing the information obtained in the detection element of the detector array assembly receiving the second split light beam and the information obtained in the detection elements of the detector array assembly receiving the one or more separated light beams of the first split light beam and for using this information to correct at least an intensity level of the first light beam being supplied to the interrogation area.

* * * * *